US 10,041,035 B2

(12) United States Patent
Salonen (10) Patent No.: US 10,041,035 B2
(45) Date of Patent: Aug. 7, 2018

(54) SYSTEM AND METHOD FOR PROCESSING BIOMASS (71) Applicant: Petteri Salonen, Tampere (FI)

(72) Inventor: Petteri Salonen, Tampere (FI)

(73) Assignee: Petteri Salonen, Tampere (FI)

( * ) Notice: Subject to any disclaimer, the term of this patent is extended or adjusted under 35 U.S.C. 154(b) by 0 days.

(21) Appl. No.: 15/511,079

(22) PCT Filed: Sep. 15, 2015

(86) PCT No.: PCT/FI2015/050613
§ 371 (c)(1),
(2) Date: Mar. 14, 2017

(87) PCT Pub. No.: WO2016/042206
PCT Pub. Date: Mar. 24, 2016

(65) Prior Publication Data
US 2017/0275583 A1    Sep. 28, 2017

(30) Foreign Application Priority Data
Sep. 17, 2014  (FI) .................................... 20145812

(51) Int. Cl.
*C05F 5/00* (2006.01)
*C12M 1/00* (2006.01)
(Continued)

(52) U.S. Cl.
CPC ............ *C12M 47/14* (2013.01); *C12M 21/04* (2013.01); *C12M 47/06* (2013.01); *C12M 47/20* (2013.01); *C05F 5/008* (2013.01); *C12M 35/02* (2013.01)

(58) Field of Classification Search
CPC ...... C12M 47/14; C12M 47/06; C12M 47/20; C12M 21/04; C12M 35/02; C05F 5/008
(Continued)

(56) References Cited

U.S. PATENT DOCUMENTS 8,153,950 B2 *  4/2012  Kiesel ...................... G01J 3/02
                                                       250/208.2
2003/0173291 A1  9/2003  Schimel
(Continued)

FOREIGN PATENT DOCUMENTS

DE        19615551 A1    12/1996
WO    WO-2007/005954 A1    1/2007
(Continued)

OTHER PUBLICATIONS

Communication of Acceptance, Finnish Patent Application No. 20145812, dated Dec. 11, 2015.
(Continued)

*Primary Examiner* — Fred Prince
(74) *Attorney, Agent, or Firm* — Marshall, Gerstein & Borun LLP (57) ABSTRACT System (100) and method for processing biomass. The system comprises a combined heat and power plant (102), an interface (114) for feeding biogas to a traffic fuel production unit, interfaces (114) to a district heating system (106a) and an electrical grid (106b), and a hydrolysis device (108), a digestion device (110), a dryer (116) and a heat recovery unit (112), which are operatively coupled for transferring heat, intermediate products and final products of the process, wherein raw biomass is received into the hydrolysis device (108), biomass processed by the hydrolysis device (108) is fed to the digestion device (110), biogas obtained in the digestion device (110) is fed to the traffic fuel production unit (104), heat is recovered from the hydrolysis device (108), biomass processed by the digestion device (110) is dried by the heat recovered from the hydrolysis device (108), heat is recovered from the dryer (116), heat recovered from the dryer (116) is fed to the hydrolysis device (108) to be used in pre-heating of the received raw biomass, heat recovered from the dryer (116) is fed to the district heating
(Continued)

(106a), and production of electricity is fueled by the dried biomass from the dryer (116).

21 Claims, 6 Drawing Sheets (51) Int. Cl.
   *C12M 1/107* (2006.01)
   *C12M 1/42* (2006.01)
(58) Field of Classification Search
   USPC ............... 210/603, 612, 613, 614, 252, 259; 585/240
   See application file for complete search history.

(56) References Cited

U.S. PATENT DOCUMENTS

| | | | |
|---|---|---|---|
| 2009/0227003 A1* | 9/2009 | Blotsky | C12M 21/02 435/257.1 |
| 2010/0041119 A1 | 2/2010 | Christensen et al. | |
| 2012/0208254 A1* | 8/2012 | Smith | C12M 21/02 435/167 |
| 2013/0087339 A1 | 4/2013 | Foody | |
| 2014/0030695 A1* | 1/2014 | Smith | C12M 41/48 435/3 |
| 2017/0107478 A1* | 4/2017 | Harmon | C12M 43/04 |
| 2017/0184015 A1* | 6/2017 | Andren | C12M 21/04 |

FOREIGN PATENT DOCUMENTS

| | | |
|---|---|---|
| WO | WO-2007/009463 A2 | 1/2007 |
| WO | WO-2009/141495 A1 | 11/2009 |
| WO | WO-2013/117686 A1 | 8/2013 |
| WO | WO-2014/082007 A2 | 5/2014 |

OTHER PUBLICATIONS

International Search Report and Written Opinion, International Application No. PCT/FI2015/050613, dated Dec. 4, 2015.
Office Action, Finnish Patent Application No. 20145812, dated May 6, 2015.
Search Report, Finnish Patent Application No. 20145812, dated May 6, 2015.
Starfelt et al., The impact of lignocellulosic ethanol yields in polygeneration with district heating—A case study, Appl. Energy, 92:791-9 (2012).
Barber et al., "Thermal Hydrolysis: The Missing Ingredient for Better Biosolids?", Water & Wastewater International magazine (Jan. 9, 2012).
"Suomessa käytettävien polttoaineiden ominaisuuksia" (Characteristics of the Fuels Used in Finland), VTT/Alakangas (2000).
European patent application No. 15842636.1, Extended European Search Report, dated Apr. 24, 2018.

* cited by examiner

SYSTEM AND METHOD FOR PROCESSING BIOMASS

CROSS-REFERENCE TO RELATED APPLICATIONS

This application is a national stage application of International Application No. PCT/FI15/50613, filed Sep. 15, 2015, which claims priority under 35 U.S.C. § 119 to Finnish Patent Application No. FI20145812, filed Sep. 17, 2014.

BACKGROUND

National Renewable Energy Laboratory (NREL) in November 2002 NREL/SR-510-33000 presented the concept of Bioethanol production plant and Combined Heat and Power (CHP) plant co-location, to utilize CHP heat and power in Biofuel production. The report presents an idea to use rest of the remaining biomass, referred as lignin, as part of the CHP fuel.

Christensen et al. defined a method and device for thermal hydralisation in patent US2010041119A Method and apparatus for conversion of cellulosic material to ethanol. The patent defines separation of lignin and co-firing it in a CHP device, which is connected to the power grid.

ST1/Ahokas et al. define a method and device for Bioethanol production in WO2009141495 (A1). The patent indicates dry matter to be used as biofuel to partly provide thermal energy to be used in hydrolyzing, fermentation, vaporization and dehydrating means.

Veolia water solutions & tech/Hoejsgaard define an apparatus for continuous hydrolysis in WO2013117686 (A1) using solid matter as fuel.

Water & Wastewater International magazine presented in the issue of Sep. 1, 2012 an example of thermal hydrolysis in actual waste water and sludge treatment. It concluded that best energy balance is reached when waste water sludge is treated with thermal hydrolysis but not dried. Dried sludge results better energy production, but requires more energy in drying process than is gained by burning less humid sludge.

VTT/Alakangas 2000 "Suomessa käytettävien polttoaineiden ominaisuuksia" (Characteristics of the fuels used in Finland) estimates the energy efficiency in bio based fuels as a function of dry mass content and effective caloric value.

Fossil fuels cause emissions that are harmful to the nature. Production of biofuels requires external energy. Production of the external energy for biofuel production decreases the efficiency of the biofuel production in terms of energy required to produce a unit of biofuel.

SUMMARY

Embodiments of include a method and a system characterized by what is stated in the independent claims. Further embodiments are defined in the dependent claims.

Some embodiments provide self-sufficient production of traffic fuel, heat and power from renewable biomass and enable the storing of the energy sources for later use as control and compensation power.

BRIEF DESCRIPTION OF DRAWINGS

In the following description embodiments will be described with reference to the following drawings, in which.

DETAILED DESCRIPTION OF EMBODIMENTS

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
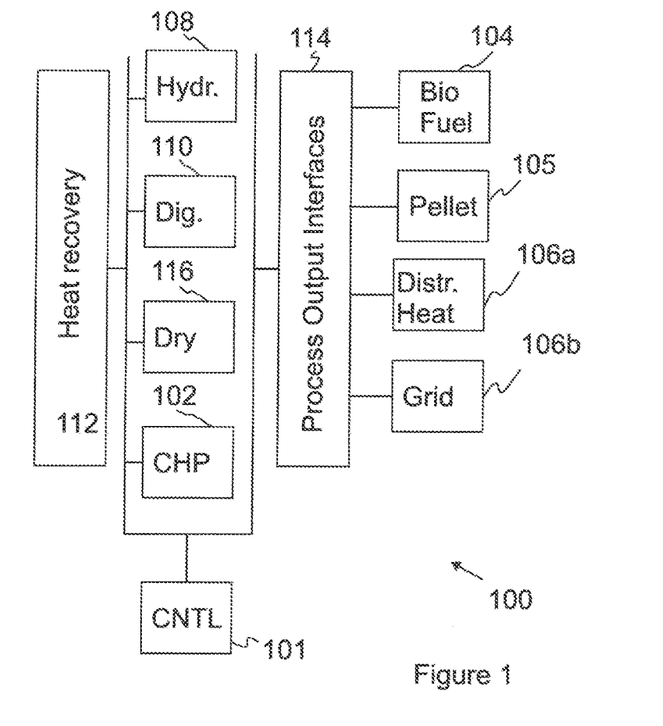
FIG. 1 illustrates an example of system according to an embodiment.

FIG. 1 illustrates an example of system according to an embodiment. The system 100 comprises a Combined Heat and Power (CHP) plant 102, an interface 114 for feeding biogas to a traffic fuel production unit 104, interfaces 114 to a district heating system 106a and an electrical grid 106b, and a hydrolysis device 108, a digestion device 110, a dryer 116 and a heat recovery unit 112, and a pellet machine 105, which are operatively coupled for transferring heat, intermediate products and final products of the process. The coupling may be achieved by structures including for example including pipes, heat transfer units and valves which are known to a skilled person. The system processes raw biomass and produces heat, electricity, biofuel and/or pellets. Preferably the biofuel is biogas processed by the traffic fuel production unit and the biogas is suitable to be used as traffic fuel in vehicles, for example cars. The system is self-sufficient such that no external energy sources are needed for processing of the biomass. It should be appreciated that the self-sufficient phase of operation may be achieved after a startup phase, where first batches of biomass are processed to obtain energy for processing the subsequent batches. The self-sufficient phase of operation may be reached after a sufficient amount of raw biomass has been processed and dried biomass, e.g. pellets, have been produced for fueling the CHP plant for generating electricity and heat for the processing of subsequent batches of biomass.

The CHP plant performs combustion of dried biomass and generation of electricity from the heat obtained in the combustion. Combustion of the biomass may be used to heat water to obtain water vapor, i.e. steam, for driving a turbine that drives an alternator or generator for generating electricity. An example of the CHP plant is described with reference to FIG. 10 below.

The digestion device produces biogas by anaerobic digestion of the biomass treated by the hydrolysis device. The digestion device may have one or more containers, where biomass is treated by anaerobic digestion. The biomass may be processed in the digestion as batches or the digestion device may be a continuous process device. Preferably each of the containers has a mixing apparatus to circulate the biomass within the container. The mixing apparatus mixes the biomass and releases methane for the biomass.

The traffic fuel production unit obtains biogas from the digestion device and refines the biogas to high grade biomethane by extracting nondesired substances from the biogas. The biogas obtained from the digestion includes $CH_4$, $CO_2$, $H_2O$, $S_2$ and other, non-desired substances. The traffic fuel production processes the biogas obtained from the digestion device and produces refined biogas conforming to national and international regulations. The refined biogas conforms to national and international regulations and has 87-98% of methane ($CH_4$). The traffic fuel production unit can be any kind of biofuel purification purpose device, including but not limited to membrane or water washtechnology based device.

The dryer obtains biomass treated by the digestion device. The dryer removes moisture from the biomass. As a result Solid BioMass (SBM) is produced. Dry matter content of the SBM can range from 40 to 95%. The dryer includes three parts:
1) a Mechanical Dryer (MD)
2) a Thermal Dryer Preheater (TDP)
3) a Thermal Dryer (TD).

The biomass is first received to the MD after which the biomass dried by the MD is conveyed to the TDP. After pre-heating the biomass in the TDP, the biomass is conveyed to the TD. Accordingly, the biomass is first dried in the MD to extract as much water as possible. One preferred device for mechanical dryer is to use screw press dryer, as it can remove the moisture up to 50% dry matter content, but other devices are acceptable providing they can remove energy efficiently a large amount of humidity. The MD may be isolated to maintain most of the thermal heat of the biomass. The SBM may be fed from the dryer to a pellet machine 105 for processing the SBM to pellets or briquettes to enable easier drying process and storing. The optional pellet machine can be co-located to the Dryer.

The TDP is a heat exchanger unit, which recovers the thermal energy included in water vapor, i.e. steam, from the biomass and then brings part of the thermal energy back to the process. It can be the type of a thermally isolated conveyor between the MD and the TD. A conveyor may be used to move the partly dried biomass from the MD to the TDP and TD. A thermal energy connection duct may recover the steam from biomass in the end of TD and transports it to the TDP, where the steam is released via a heat exchanger. The humidity in the steam is may be returned back to the process after TDP.

The TD comprises of:
1) a steam collection duct between the hydrolysis device and the TD
2) a Dryer unit which establishes a thermal connection to the biomass, like rotary dryer, belt dryer or similar releasing the heat to the partly dried biomass
3) a collection duct to return dryer steam to the TDP.

The heat recovery unit is a thermal energy collection and circulation system providing recovery and feed of heat from one part of the system to another part. The heat recovery unit provides a self-sufficiency of the system such that external power sources are not needed at least after the startup phase of the system and when the is operating continuously. The heat recovery unit may be formed by ducts that collect and feed steam between parts of the system, for example between the hydrolysis device and the TD and within the hydrolysis device. The structure of the dryer described above is illustrated in FIG. 5, where operation of the dryer in processing biomass may be referred to for details.

The hydrolysis device performs hydrolysis of biomass. In hydrolysis, biomass is mixed with water and water vapor, i.e. steam, for sterilization and hydrolysis. The hydrolysis device includes one or more heated and pressurized container units capable of handling over 15 bar operating pressure. The containers are, thus suitable for heating biomass over 200° C. for the sterilizing and hygienization of the biomass. In hydrolysis, water is used to break carbohydrates to smaller parts. In this way, the biomass treated in the hydrolysis device may be easier and faster turned into biogas in the digestion device than if no hydrolysis was performed. Hydrolysis temperatures and pressures vary depending on the biomass in question. Results obtained by experiments have shown that a temperature of 200° C. is enough to provide hydrolysis to most of the biomass. The structure of hydrolysis containers is discussed in more detail in FIG. 3.

In an embodiment the hydrolysis device and digestion device may be implemented in a single device depending on the size of the anaerobic digestion system, the system size and desired control points of the process. The same container may be used to perform hydrolysis and digestion of the biomass. Accordingly, the hydrolysis may be one of the four phases of anaerobic digestion: Hydrolysis, Acidogenesis, Acetogenesis and Methanogenesis.

In an embodiment, locations of the containers in the digestion device may be arranged differently on the basis of the phase of anaerobic digestion performed in the container such that efficiency of the biological process may be provided. As an example, Acidogenesis can be run in a cooler container than Acetogenesis and Methanogenesis. Accordingly, a container performing Acidogenesis may be located in an area that is less heated and/or has a lower thermal insulation, than a container performing Acetogenesis or Methanogenesis.

A controller 101 may be connected to the devices in the system for monitoring and controlling the process. The controller may be connected to one or more sensors, the sensors comprising for example one or more from a group comprising a humidity sensor, a weight sensor, a pH-sensor and/or a pressure sensor, a temperature sensor operatively coupled to one or more of the hydrolysis device, the heat recovery unit, the digestion device, the dryer and the interfaces, for monitoring corresponding limits in batches of biomass processed by the system.

Figure 2:
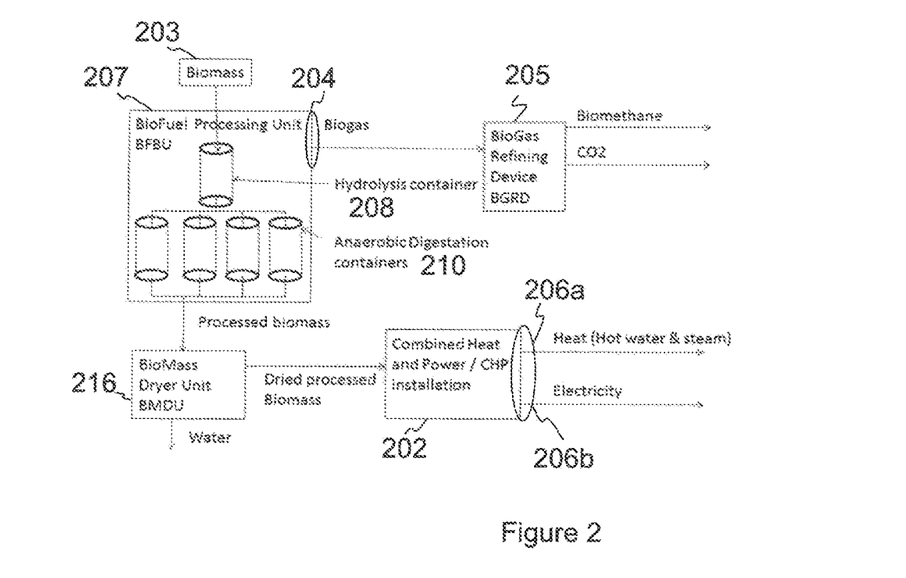
FIG. 2 illustrates an example of material flow in a system according to an embodiment.

FIG. 2 illustrates an example of material flow in a system according to an embodiment. The system may be the system illustrated in FIG. 1. In 203, raw biomass is received to the system for processing. The biomass may be first treated in a BioFuel Processing Device (BFPD) or BioFuel Processing Unit 207 that performs sterilization and anaerobic digestion of the biomass. The anaerobic digestion may be performed in several phases, where some of the phases may have dedicated containers as described above for the hydrolysis device 208. In the following the material flow is described with separate containers (in FIG. 2 only one container described) for hydrolysis in a hydrolysis device 208 and further phases of the digestion, the Acidogenesis, Acetogenesis and Methanogenesis in a digestion device 210. The hydrolysis device 208 and the digestion device 210 may be included in the BFPD. The hydrolysis device has one or more containers, where each container performs hydrolysis of the raw biomass. Biomass processed by the hydrolysis device is fed to the digestion device 210. The digestion device includes one or more containers, where anaerobic digestion of the biomass is performed.

The digestion produces biogas and digested biomass. The digested biomass is fed to a dryer 216 and the biogas obtained from the digestion device is fed to a traffic fuel production unit 205 via an interface 204. In the dryer water is removed from the biomass and Solid BioMass (SBM) is produced. In the traffic fuel production unit the biogas is refined to traffic fuel, for example bio-methane. As a bi-product the traffic fuel production unit may produce Carbon Dioxide, $CO_2$. The SBM is fed from the dryer to a CHP plant 202 where the SBM is burnt, whereby and electricity and heat is produced. The electricity may be fed to an electrical grid for distribution via an interface 206a, and the heat may be fed to a district heating system via an interface 206b. The heat may be transferred to the district heating as hot water, water vapor, i.e. steam, or any other medium suitable for heat transfer.

Figure 3:
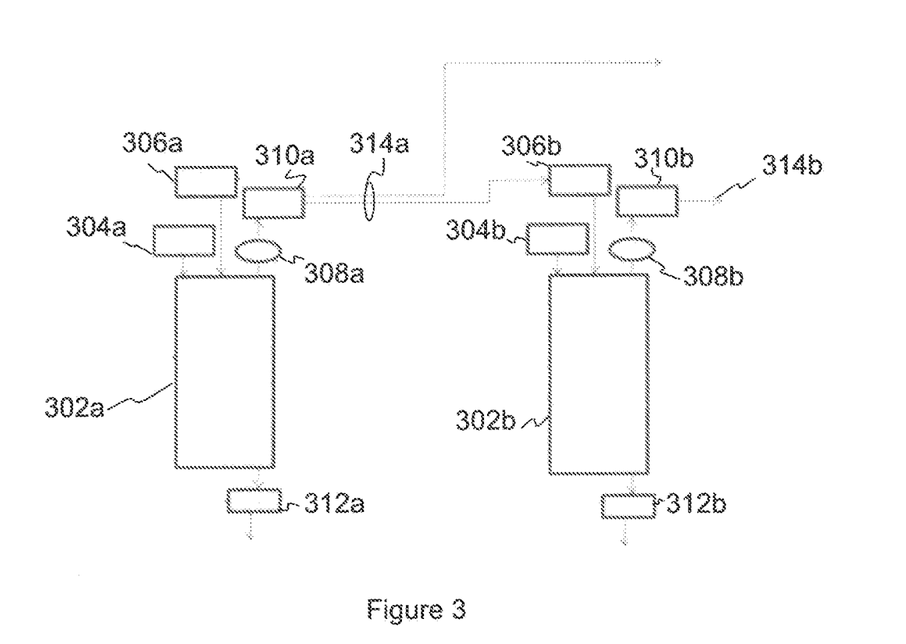
FIG. 3 illustrates an example of hydrolysis device according to an embodiment.

FIG. 3 illustrates an example of hydrolysis device according to an embodiment. The hydrolysis device may be installed to the system of FIG. 1. The hydrolysis device may include a plurality of containers 302a, 302b such that a plurality of batches of raw biomass may be processed simultaneously. Each batch may be processed in a plurality of phases. In this way output of processed biomass from the hydrolysis device may be increased and energy efficiency of the hydrolysis may be provided. The energy efficiency may be provided by the transfer of heat between batches that are in different phases of the hydrolysis.

The hydrolysis device may include input valves 306a, 306b for feeding heat to the containers. The heat may be in the form of water vapor, i.e. steam. In different phases of the hydrolysis the input valves may be controlled to feed heat from the CHP or from another hydrolysis container. The heat from the CHP may be obtained in different temperatures depending on whether the steam is obtained after or before a turbine. Steam after turbines may have a lower temperature, approximately 125° C., than temperature of the steam from a boiler before the turbines, approximately 500° C.

Input valves 304a, 304b allow feeding water and raw biomass to the containers. Output valves 310a, 310b allow feeding excess heat out of the containers to be utilized in other parts of the system or in another hydrolysis container. In FIG. 3, the heat transferred out of the containers is illustrated by arrows 314a, 314b. The heat may be utilized for example in the dryer. On the other hand, the heat may be fed within the hydrolysis device to another hydrolysis container. In this way, when hydrolysis is performed in successive phases for a plurality batches, batches that are being processed in different phases may exchange heat such that excess heat from one phase being treated in one container 302a may be transferred to another phase being treated in another container 302b, where more heat may be required.

A steam dome 308a, 308b may be installed between the output valve and the container. The steam dome receives water vapor, i.e. steam, from the container and reduces the pressure of the steam such that the hot process biomass from the container is prevented to enter the steam output valve and towards other parts of the system or another hydrolysis container. Since the pressure is reduced, solid biomass may remain upwards, e.g. in the container and/or in the steam dome, with respect to the flow direction of the steam from the container to the output valve.

Containers have output valves 312a, 312b to allow transfer of processed biomass to the digestion device.

The hydrolysis device of FIG. 3 may be used in a method for sterilization and hydrolysis of biomass according to an embodiment. The method comprises three phases that may be performed by each of the containers:

1) In the first phase the biomass in container 302b is heated with the thermal energy from the CHP device steam. The biomass is heated up to 120-125° C., depending of the CHP steam output temperature after electricity generating turbine.
2) In the second phase the biomass in the container 302b is heated by recovering the heat from the third heating phase in the container 302a. The temperature is risen in the container 302b between 140-160° C., depending on the temperature of the third phase heated biomass (165-200° C.). The biomass temperature will roughly be the average of the first and third phase.
3) In the third phase the biomass in the container 302b is heated with very hot steam (>+200° C.) from the CHP process before turbines and it raises the temperature of the biomass to a level between 165-200° C. for the final hydrolysis and sterilisation temperature. The final temperature depends on type of biomass to be treated and the wished processing temperature.

After the third phase of hydrolysis is complete, the hydrolysis container may be emptied by opening the steam output valve 310b, and after opening the steam output valve, the biomass output valve 312b may be opened for transferring the biomass from the hydrolysis container to the digestion device. The steam dome prevents the processed biomass from entering the steam output valve 310b.

In the hydrolysis described above referring to FIG. 3, the hydrolysis containers are connected such that thermal energy, e.g. heat or water vapor, i.e. steam, may be recovered from the third phase of the batch processed in one hydrolysis container to another hydrolysis container for heating phase 2. The connection between the containers may be provided by a duct that may be a part of the heat recovery unit of the system.

In optimal application with adequate heat conduction time, a half of the recovered thermal energy may be transferred to the hydrolysis phase 2 in one container from the hydrolysis phase 3 another container. In certain installations, the exhaust fumes from the CHP device can be utilised also in heating of the phase 2 of the hydrolysis.

Figure 4:
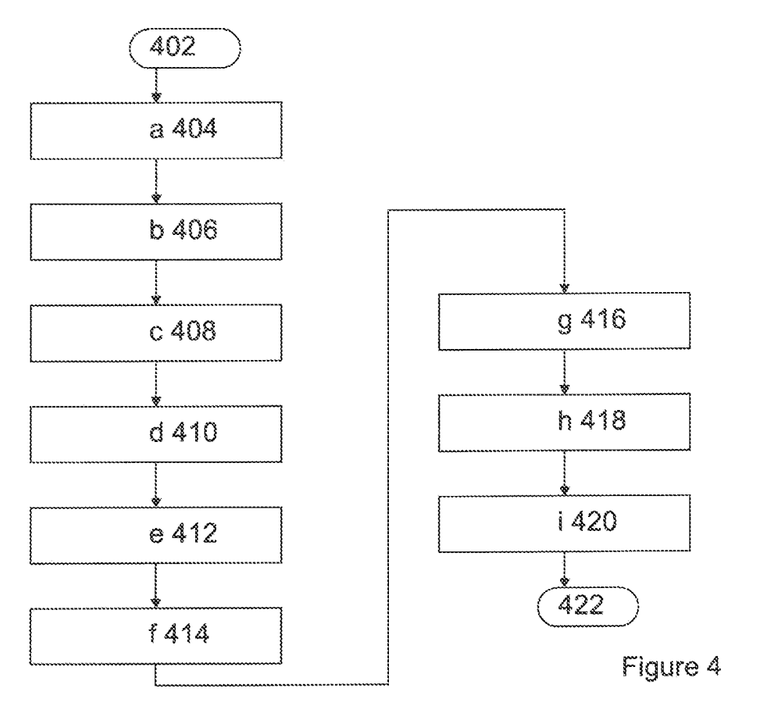
FIG. 4 illustrates an example of method according to an embodiment.

FIG. 4 illustrates an example of method according to an embodiment. The method may be performed by system illustrated in FIG. 1. The hydrolysis device may be according to the example of FIG. 3. The method may produce a material flow illustrated in FIG. 2.

The method may start 402, when the system is in a self-sufficient phase of operation. The self-sufficient phase of operation may be achieved after a startup phase, where first batches of biomass are processed to obtain energy for processing subsequent batches. The self-sufficient phase of operation may be reached after a sufficient amount of dried biomass, e.g. pellets, have been produced to fuel the CHP plant for generating electricity and heat for the processing of the subsequent batches of biomass.

In 'a' 404, raw biomass may be received into the hydrolysis device. Preferably the received biomass is pre-processed. The pre-processing may comprise removing any excess material, e.g. stones and sand, and/or cleaning and crushing the biomass. A water bed may be used to clean the biomass. A suitable crushing device may be used to crush the biomass into a desired particle size.

The biomass may comprise waste biomass from a bio-ethanol production process and biodiesel production from Algae or Oil plants, where oil is extracted from the plant by applying pressure to the biomass. The biomass may also comprise animal based biomass, for example manure and animal remains.

The hydrolysis may be a thermal hydrolysis process, where temperature of the biomass is raised to a level between 160 to 180 degrees Centigrade. High pressure may also be utilized. The hydrolysis may include hygienization of the biomass. The hygienization may be achieved by setting temperature of the biomass to 70 degrees Centigrade for 60 minutes. The hydrolysis process may include several phases, for example as described above in connection with FIG. 3.

In hydrolysis using three phases, heat is fed to a batch as controlled by measurements of temperature and time against target values of the temperature and time of each phase, whereby the batch is transferred from a current phase to a new phase on the basis of the target values of the temperature and time being met for the current phase. The heat, steam and water for the hydrolysis may be obtained from the CHP.

In 'b' 406, biomass processed by the hydrolysis device may be fed to the digestion device. In the digestion device the biomass undergoes anaerobic digestion. The digestion may be performed in one or more containers that each performs one or more phases of the anaerobic digestion process. Phases of the anaerobic digestion process comprise: Hydrolysis, Acidogenesis, Acetogenesis and Methanogenesis. The hydrolysis device and digestion may be performed in a single container as described above, whereby the steps 404 and 406 may be combined. However, if hydrolysis is performed in a separate device, the remaining phases of the anaerobic digestion may be performed, thus the Acidogenesis, Acetogenesis and Methanogenesis.

Figure 11:
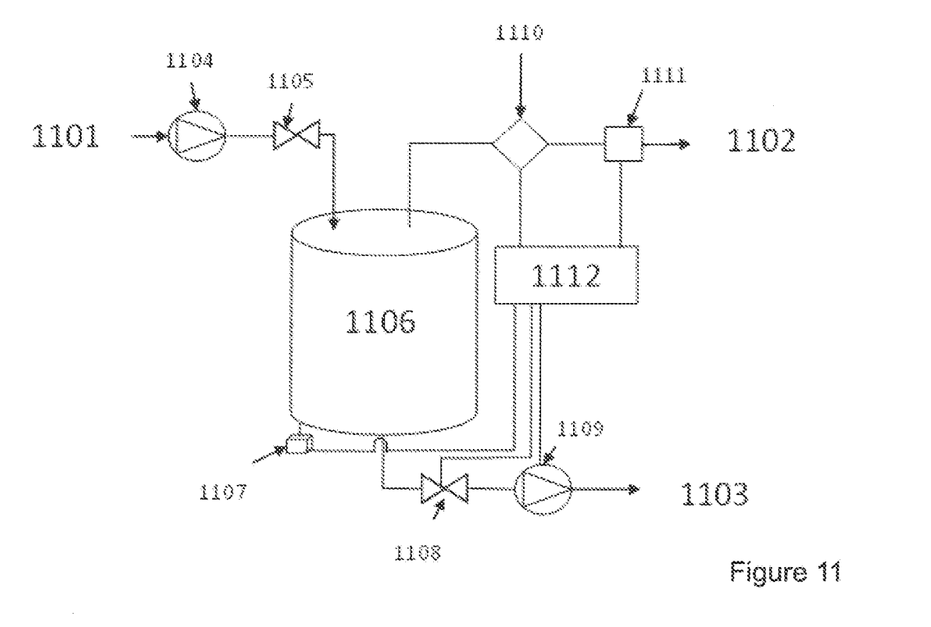
FIG. 11 illustrates a system and method for controlling digestion according to an embodiment.

In an example, the digestion device is a closed vessel or container where part of the biomass turns to biogas. It is a vessel capable of holding liquid or semisolid biomass. It has one inlet connection for biomass in, one output for biogas out and one output for digested biomass out. FIG. 11 illustrates an example of the digestion device.

Preferably the digestion is thermophilic. This may be achieved by maintaining the temperature between 50-55° C. On the other hand, other anaerobic digestion processes may be applied to the biomass. One example of an anaerobic digestion process is a mesophilic process. In the mesophilic process the process temperature of 34° C. may be maintained.

In 408 'c' biogas obtained in the digestion device may be fed to the traffic fuel production unit.

In 410 'd', heat may be recovered from the hydrolysis device.

In 412 'e', biomass processed by the digestion device may be dried by the heat recovered from the hydrolysis device. The remaining biomass that is not transformed into biogas in the degustation device may be fed from the digestion device to the dryer. The biomass may be dried into Solid BioMass (SBM) for utilization in the energy production in a CHP device.

In 414 'f', heat may be recovered from the dryer.

In 416 'g', heat recovered from the dryer may be fed pre-heating of the received raw biomass.

In 418 'h' heat recovered from the dryer may be fed to the district heating (106a).

Figure 10:
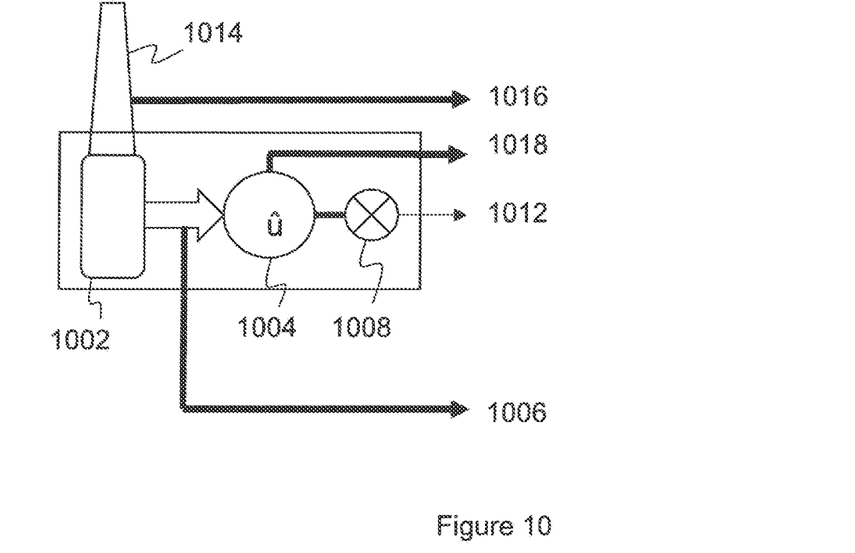
FIG. 10 illustrates an example of a combined heat and power plant for a system according to an embodiment.

In 420 'i' production of electricity may be fueled by the dried biomass from the dryer. The electricity may be produced in the CHP from combustion of the dried biomass. Heat may be recovered from the CHP prior to the heat, e.g. steam, entering the turbine and/or after the heat has travelled through the turbine. Heat prior to the turbine is hotter than the heat after the turbine. The recovered heat may be fed to hydrolysis, digestion, drying and/or district heating. Heat recovery is shown in FIG. 10 illustrates an example of a combined heat and power plant.

Potassium and phosphorus can be collected from ashes of the dried biomass after it has been combusted in the CHP device. It is assumed that most of the harmful compounds are destroyed in the combustion process due high temperatures (700-800° C.). The ashes may be used as fertilizers.

In 422, the method ends after heat from the CHP, hydrolysis device and/or dryer has been recovered and utilized in pre-heating, digestion, drying and/or for district heating. The method ends after dried biomass has been produced for fueling production of electricity by the CHP. The heat produced by the CHP may be utilized in hydrolysis, digestion, drying and/or the district heating. Electricity may be used to power the traffic fuel production unit.

It should be appreciated that the above method may be performed continuously in a system, for example the system in FIG. 1, when the system is in a phase of continuous operation, where at least one batch of biomass has been dried for fueling the CHP. Accordingly, the method may be repeated during operation of the system and the steps of the method may be performed anew. In this way a plurality of batches of biomass may be treated and energy obtained from a received batch may be used to process subsequently received batches of biomass. Preferably a system performing the method treats each batch of raw biomass such that heat, dried biomass, electricity and traffic fuel may be obtained from the raw biomass. The dried biomass may be pelletized for utilization in the CHP.

Figure 5:
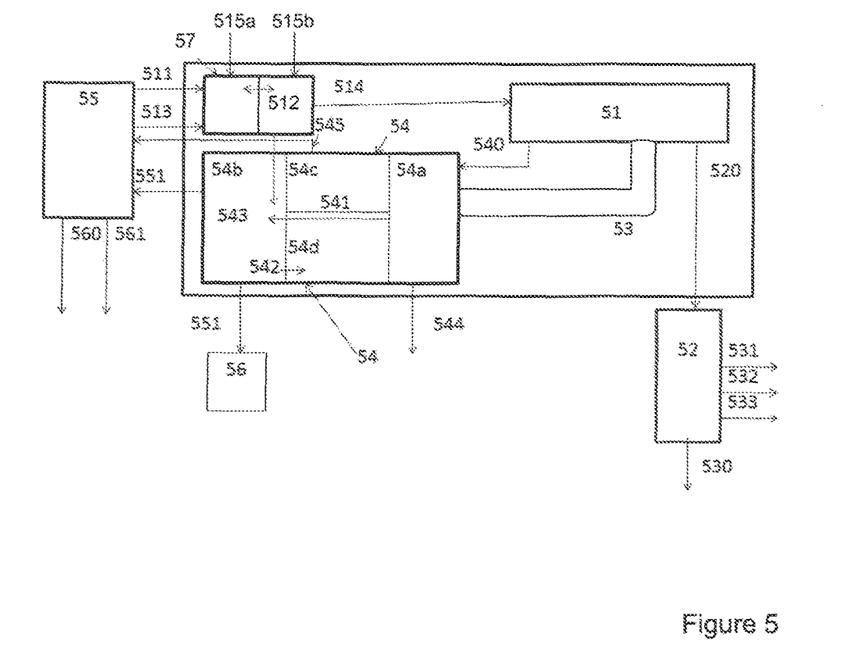
FIG. 5 illustrates an example of process schematics in a system for self-sufficient energy production according to an embodiment.

FIG. 5 illustrates an example of process schematics in a system for self-sufficient energy production according to an embodiment. In the described process schematics raw biomass is processed by a system comprising a CHP 55, a hydrolysis device 57, a digestion device 51, a traffic fuel production unit 52, a dryer 54, a hydrolysis device 57 that may be configured according to the system in FIG. 1. Thus the CHP 55, hydrolysis device 57, digestion device 51, traffic fuel production unit 52 and dryer 54 may correspond to the CHP 102, hydrolysis device 108, digestion device 110, traffic fuel production unit 104 and dryer 116 in FIG. 1. The material flow in system may be as described in FIG. 2. The hydrolysis device may be implemented as described in FIG. 3. The process schematics may implement the process of FIG. 4.

The process schematics illustrates as process as follows:

Raw biomass 515a, 515b is received in the system. Preferably the raw biomass is pre-treated, e.g. crushed biomass and mixed with water and water vapor, i.e. steam 511, 513 from the CHP and delivered to the BioFuel processing unit for hydrolysis and sterilization. The biofuel processing unit may refer to the hydrolysis device or a unit combining both the functionalities of the hydrolysis device and the digestion device.

In the biofuel processing unit the sterilization and hydrolysis takes place in three phases, as described in FIG. 3:

A) The first phase of the hydrolysis and sterilization is to heat the biomass with the heat 511 from the CHP.

B) The second phase of the hydrolysis and sterilization is heating the biomass with heat 512 recovered from the biomass after third phase heating.

C) The third phase of biomass hydrolysis and sterilization is heating the biomass with the very hot steam from the CHP 513.

After the hydrolysis and sterilization the sterilized biomass 514 is delivered to the digestion device. Biogas is produced in the digestion device by the process phases of Acidogenesis, Acetogenesis Methanogenesis. After the process phase of Methanogenesis, the results or the process are Biogas 520 and Processed Biomass 540.

Biogas 520 is delivered to the traffic fuel production unit 52, where the Biogas 520 is refined to high-grade methane, the Biome thane fuel 530. Carbon dioxide 531, water 532 and other non-desired substances like sulfur 533 are removed from the biogas 520.

The processed biomass 540 is collected and transferred to the Dryer Unit. The biomass is first dried in a Mechanical Dryer 54a resulting Partly Dried BioMass 541 and Nutrient rich reject water 544.

Partly Dried Biomass 541 is transferred to Thermal Dryer 54b via thermally isolated conveyor 54c located in a Thermal Dryer Preheater 54d. Dryer Steam 542 is transferred from Thermal Dryer 54b to the Thermal Dryer Preheater 54d where it warms up the Partly Dried Biomass 541 before Thermal Dryer 54b. Steam and condensed water 545 is returned to the process.

In Thermal Dryer 54b Partly Dried Biomass 541 is heated with water vapor, e.g. steam 543 from the BFPD 57 forming SBM 551 and Dryer Steam 542.

The SBM 551 can be stored in SBM storage 56 and used as fuel in the CHP plant 55 to be burned to produce energy in the forms of hot water and steam 560, which can be further utilized to produce electricity 561.

The system may comprise short-cut piping 53 for connecting the digestion device and the mechanical dryer. In a case of batch contamination, the contaminated batch will be directed to the dryer via the short-cut piping. In this way the contaminated container in the digestion device may be sterilized and washed with hot water 560 from the Combined Heat and Power device 55.

Figure 6:
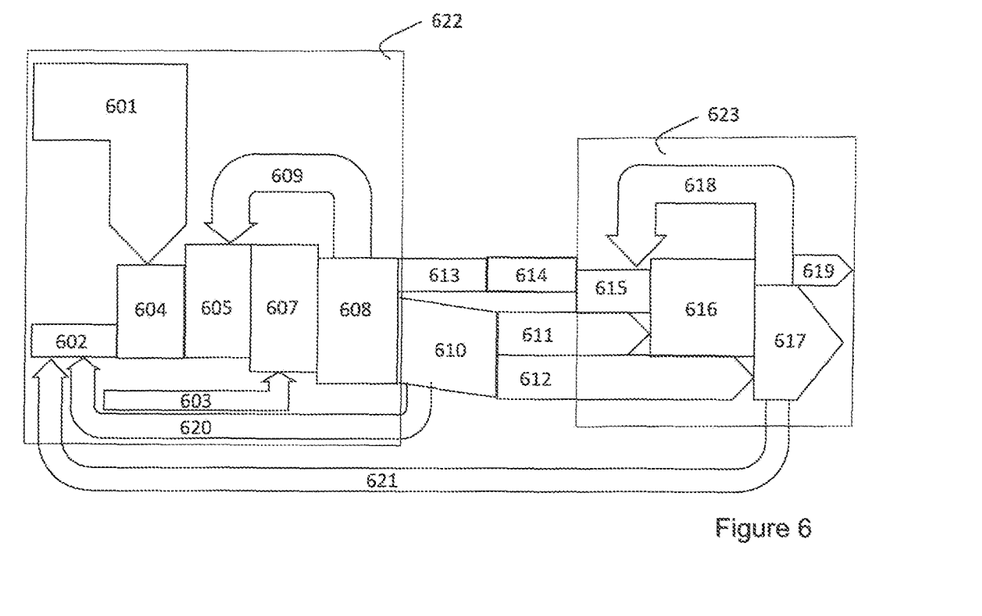
FIG. 6 is an example of energy flow in a system according to an embodiment.

FIG. 6 is an example of thermal energy flow in a system according to an embodiment. The thermal energy flow is described with reference to heat but the thermal energy may also be hot water or steam, i.e. water vapor. The thermal energy flow is described with reference a hydrolysis device 622, and a thermal dryer 623 that correspond to the hydrolysis 108 device, dryer 116 and digestion device 110 in FIG. 1. The hydrolysis device may be structured as described in FIG. 3. The structure of the dryer may be as described in FIG. 5.

In 601, heat is received from CHP to the hydrolysis device 622. The hydrolysis may be performed in three phases 604, 605, 607. The heat from the CHP may be used to heat biomass received to the hydrolysis to a desired temperature for the first phase 604 of hydrolysis. Heat after the last phase 607 hydrolysis, from a batch 608 processed by the hydrolysis device, may be fed 609 to the second phase 605 of the next batch processed by the hydrolysis device. The third phase of the hydrolysis may receive heat 603 from the CHP. The heat 601 from the CHP to the first phase may be recovered after the turbines in the CHP, whereas the heat 603 to the third phase may be recovered from the CHP before the turbines.

The hydrolysis may produce excess heat 610 that is not utilized within the hydrolysis device. The excess heat may be fed 620 to pre-heat the biomass 602 received to the hydrolysis device. On the other hand, the excess heat may be fed 611, 612 to be utilized in the thermal dyer and/or in district heating. Some 611 of the excess heat may be utilized in the thermal dryer, and some of the excess heat may be utilized in district heating. If the excess heat is not utilized in the thermal dryer or district heating, the excess heat may be fed 621 to pre-heat raw biomass 602 before the hydrolysis.

On the other hand the excess heat 610 may additionally or alternatively be fed 611 to the thermal dryer to be used in drying the biomass. On the other hand the excess heat 610 that is not utilized in the thermal dryer 623 may be fed 621 to the hydrolysis device to be used in drying the biomass.

The anaerobic digestion consumes some thermal energy 613. Also mechanical drying of digested biomass consumes thermal energy 614.

In the thermal dyer 623, heat recovered from the hydrolysis device, the CHP, the digestion device and the thermal dryer 616 may be recovered and utilized 618 in the thermal pre-dryer 615 or fed to pre-heat the biomass received in the hydrolysis device. Some thermal energy may be left in solid biomass 619.

It should be appreciated that the CHP produces electricity that may be used to power operations in the system, including pre-processing of the biomass, circulating biomass in the digesting device, production of pellets, production of the traffic fuel and automation of the process, for example operating valves and conveyor belts. Excess electricity may be fed to the electrical grid.

Figure 7:
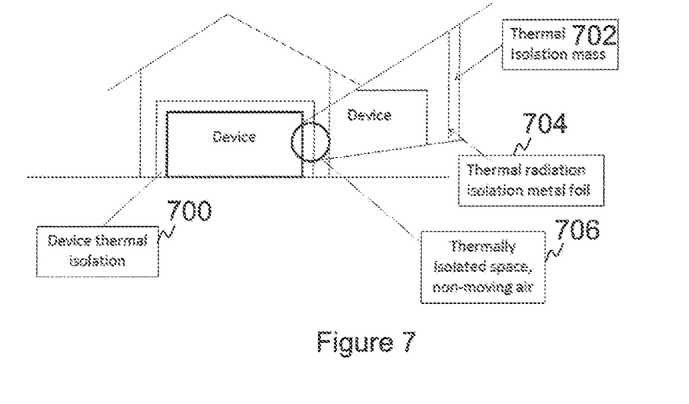
FIG. 7 illustrates an example of thermal isolation in a system according to an embodiment.

FIG. 7 illustrates an example of thermal isolation 700 in a system according to an embodiment. The thermal isolation may comprise thermal isolation mass 702 and thermal radiation isolation 704. The isolation mass may be mineral wool for example. The radiation isolation may be a metal foil. The system or parts of the system may be isolated by the thermal isolation and located in a thermally isolated space 706 with non-moving air acting as isolation.

The system may be the system described in FIG. 1. The thermal isolation may be used to isolate one or more parts of the system illustrated in FIG. 1. Accordingly each part of the system may be isolated by a three-layer isolation comprising 1) An isolation mass layer to reduce heat conduction, 2) A metal foil layer to return thermal radiation back to the device, 3) Isolation layer in the form of non-moving air.

An embodiment concerns a method of upgrading an existing CHP plant. Now referring to items in FIG. 2, the BFPD 207, the traffic fuel production unit and the dryer may be combined with an existing CHP device. In this way the biomass may be treated to fuel the production of electricity and heat in the CHP. A conventional fossil fuel CHP may be converted into a CHP operated by renewable energy and a production plant of renewable traffic fuel.

Figure 8:
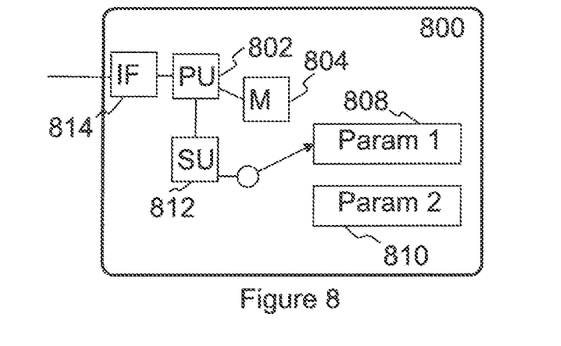
FIG. 8 illustrates an example of a controller for a system according to an embodiment.

FIG. 8 illustrates an example of a controller 800 for a system according to an embodiment. The controller 800 may be the controller in the system of FIG. 1. The controller includes an interface unit 814 for communications with devices of the system and one or more of sensors, valves, and conveyor belts. A Processing Unit (PU) 802 is connected to the interface unit for communications with the system. A memory 804 and a selector unit 812 may be connected to the processing unit. The memory may store instructions for execution by the processing unit. The processing unit may operate the communications unit and selector unit as instructed by the instructions for controlling recovery of heat, control flow of material and monitor parameters of the system.

The communications may be wired or wireless. Wired connections may be implanted by electrical wiring, for example as an Ethernet connection or a field bus for example Profibus. Wireless connections may be implemented for example using IEEE 802.11 based wireless local area connections.

The selector unit may select parameters 808, 810 to be used in the system for processing biomass. The parameters may include one or more values of temperature values, humidity values, pH-values, pressure values and/or weight values for different part or phases of the processing of the biomass. The selector unit may perform the selection of parameters to be used based on a type of the biomass being processed. Also information obtained from sensors may be used to determine characteristics of heat flow between at least one of: parts of the system and batches of biomass processed by the system. The characteristics of the heat flow may be used in determining parameters in the system.

It should be appreciated that connections between the units in the controller may be electrical connections and one or more of the units may be combined into a single unit or functionalities of a particular unit may be divided between other units.

The selector unit, controller and the interface unit may be provided as separate units or they may be integrated into a single unit. Memory may be provided in each of the units as necessary to store information including but not limited to process parameters, weight values, pH-values, temperature values and pressure values and computer program code. Separate units may communicate over wired and wireless connections as described above. Units may also be implemented in a computer, expansion bus cards, circuitry, a chip, a processor, a micro controller, or their combination.

Figure 9:
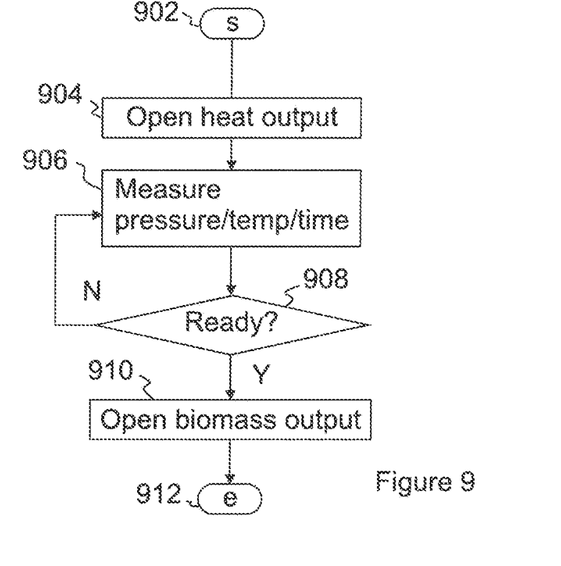
FIG. 9 illustrates an example of a method for controlling a system according to an embodiment.

FIG. 9 illustrates an example of a method for controlling a system according to an embodiment. The method may be performed by the controller in the FIG. 1. The controller may be implemented to the description in FIG. 8. The method may start 902, when the controller is installed to a system for processing biomass. An example for the system is illustrated in FIG. 1. The system has preferably reached an operation phase, where it is operating self-sufficiently, or at least one hydrolysis container has reached final phase of the hydrolysis. The hydrolysis may have three phases as described above.

In 904, a heat output valve of the hydrolysis container is opened. The heat output valve may be the heat output valve connected to a heat recovery unit. Heat is released from the container through the output valve. The heat may be transferred to another hydrolysis container, to a digestion device, to the dryer or to district heating via a heat recovery unit.

In 906, temperature and/or pressure of the hydrolysis container may be measured. A temperature sensor and/or a pressure sensor may be installed to the hydrolysis container to measure the temperature or pressure inside the hydrolysis container. Elapsed time may also be measured. The time may be measured with respect to one or more events in the process. An event may be the opening of the heat valve in 904. Accordingly one or more of the temperature, time and pressure may be measured, and the measurements may be made continuously or as triggered by an event, for example the opening of the heat valve.

If in 908 the measured values of time, pressure, and/or temperature exceed a threshold set for a corresponding value, the method may proceed to 910, where a biomass output valve is opened for transferring the biomass to the digestion device. A threshold value for the time, pressure and temperature may be set by experiments such that efficiency of the heat recovery from the hydrolysis container may be kept high while optimizing yield of the process measured as process biomass per time unit. If in 908 a set threshold is not exceeded, the method continues to 906.

In an embodiment, the biomass output valve may be opened after determining a decrease of pressure level within the hydrolysis device below a threshold value for the pressure. In this way flow of biomass out of the hydrolysis container may be kept under control and avoid danger to personnel that may be nearby.

In 912 the process may end after the biomass has been removed from the hydrolysis container. After, this the hydrolysis container may be reloaded with a next batch of biomass which may be processed in phases. In the final phase of the hydrolysis of the next batch, the method may be performed again from 902.

FIG. 10 illustrates an example of a combined heat and power plant for a system according to an embodiment. The CHP plant comprises a boiler 1002, a turbine 1004, a generator 1008 and a chimney 1014. The CHP plant may be a part of the system illustrated in FIG. 1. FIG. 2 illustrates a material flow of the system. The material flow may be obtained as part of the process described in FIG. 4. Dried biomass processed by the system is burnt in the boiler and exhaust gases from the boiler may be fed to the chimney. The dried biomass may be pelletized before burning. The boiler produces steam, i.e. water vapor that is fed to the turbine driving the generator for producing electricity 1012. The CHP plant may include necessary means including ducts, piping and valves for recovering thermal energy in the form of exhaust gases 1016 from the boiler and/or steam 1006, 1018 from the turbine to a hydrolysis device, a digestion device and a thermal dryer in the system. When the CHP plant includes more than one turbine, thermal energy 1006 may be recovered before the last turbine and/or thermal energy 1018 may be recovered after the last turbine. In this way, for a high demand of thermal energy, steam 1006 may be recovered after being used to drive at least one turbine, but before the steam enters the last turbine. On the other hand if the demand for thermal energy is low, the steam 1018 may be recovered after all the turbines in the CHP plant. The described CHP planet provides that the amount of thermal energy fed for processing the biomass in the hydrolysis device, digestion device, and the dryer may be adapted.

Present apparatuses comprise processors and memory that can be utilized in an embodiment. For example, the controller, interface unit and selector unit may be software applications, or modules, or units configured as arithmetic operations, or as programs (including an added or updated software routine), executed by an operation processor. Programs, also called program products, including software routines, applets and macros, can be stored in any apparatus-readable data storage medium and they include program instructions to perform particular tasks. All modifications and configurations required for implementing functionality of an embodiment may be performed as routines, which may be implemented as added or updated software routines, application circuits (ASIC) and/or programmable circuits. Further, software routines may be downloaded into an apparatus. The apparatus, such as a controller or a corresponding controller module may be configured as a computer or a microprocessor, such as single-chip computer element, including at least a memory for providing storage area used for arithmetic operation and an operation processor for executing the arithmetic operation. An example of the operation processor includes a central processing unit. The memory may be removable memory detachably connected to the apparatus.

FIG. 11 illustrates a system and method for controlling digestion according to an embodiment. The digestion may be anaerobic digestion performed in the digestion device in the system of FIG. 1. The system and method of FIG. 11 may provide controlling the degree of anaerobic digestion. In the system and method a weight of the batch processed by the digestion device and humidity of the biogas output from the digestion device are measured for determining termination of the digestion of the biomass.

Controlling the degree of digestion may be used to control the amount of produced biofuels, the traffic fuel as biomethane and solid biofuel for heat and power production. In favor of more solid biofuel production to produce more heat and power, the anaerobic digestion will be interrupted before all digestible biomass has been turned into biogas. To secure self-sufficient operation, enough solid biomass need to be produced to provide enough thermal energy for the process. It may also be wished to control the amount of biogas and solid biofuel because of economic situations, for example in winter in colder climate, there will be need for more electricity and thermal energy than traffic fuel and then it is economically beneficial to produce more solid biofuel and less biogas.

The amount of produced solid biomass is controlled by the amount of digested biomass 1103 coming out of the Anaerobic Digestion device 1106. Biomass 1101 is pumped in by input pump AD 1104 via input valve AD 1105 to the AD device 1106, where the biomass is digested. The digestion results are biogas 1102 and digested biomass 1103. To set the time point where the process has reached degree of digestion and desired amount of digested biomass 1103 is available, the control unit 1112 monitors the weight change of biomass in the AD device 1106, measured by a weight sensor 1107, added with the mass of water vapor in biogas out 1102 either as a function based on information from gas volume meter 1110 and information from humidity measure 1111 or weighting the water amount in biogas by other means.

As an example, the batch weight of biomass in 1101 is 1000 kg, and the dry matter weight of batch is 100 kg, from that information we know that the amount of water, $m_{water\ biomass\ in}$, is 900 kg. We set the desired amount digested biomass out, $m_{digested\ biomass\ out}$, to be 55% equaling 55 kg in the batch. At the time point where mass information, $m_{AD\ batch}$, from weight sensor 1107 is 945 kg, and the water in biogas out, $m_{water\ in\ biogass\ out}$, 1102 is 10 kg measured by the information form the gas volume meter 1110 and humidity measure 1111 device, the batch is ready and can be moved from the AD device 1006 controlled by control unit 1112 operating the output pump AD 1109 and opening the output valve 1108. The dry matter content in biomass batch is:

$$m_{digested\ biomass\ out} = m_{AD\ batch} + m_{water\ in\ biogas\ out} - m_{water\ in\ biomass\ in}$$

$$m_{digested\ biomass\ out} = 945\ kg + 10\ kg - 900\ kg$$

$$m_{digested\ biomass\ out} = 55\ kg.$$

Figure 12:
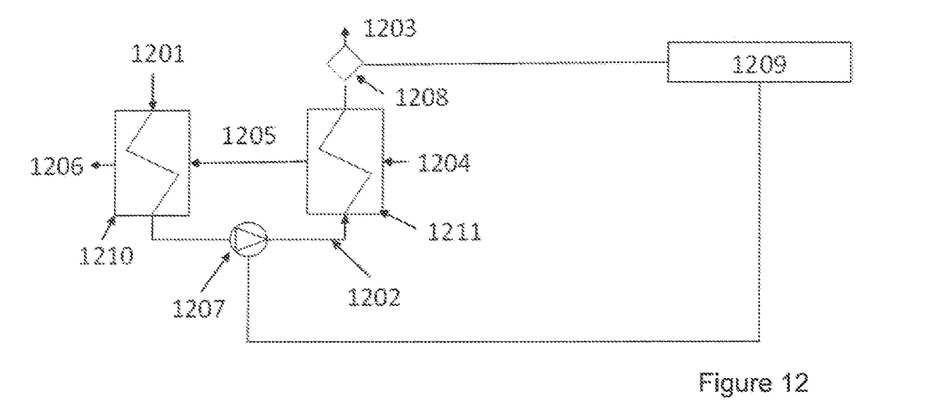
FIG. 12 illustrates recovering thermal energy for hydrolysis, according to an embodiment.

FIG. 12 illustrates recovering thermal energy for hydrolysis, according to an embodiment. The recovery of thermal energy may be performed in the system of FIG. 1. The thermal energy may be recovered from the biomass processed by a hydrolysis device. The hydrolysis device may be the hydrolysis device in FIG. 3. Accordingly, heat may be recovered from a batch of biomass removed from hydrolysis device after being processed by the hydrolysis device. A next batch of biomass may be heated by the recovered heat from the heat recovered from the processed batch of biomass. When heat is transferred from the processed batch to the next batch to be processed by the hydrolysis device, the processed batch of biomass is cooled and may be fed to a digestion device.

The thermal recovery may be performed by a heat exchanger unit. The heat exchanger unit may comprise a twin heat exchanger assembly in order to cool down the hydrolyzed biomass more efficiently than just by one heat exchanger. Also more heat can be used in biomass preheating before hydrolysis. Thermal energy from the hydrolysis is recovered by running the hydrolyzed biomass 1201 via heat exchanger A 1210 where the hydrolyzed biomass 1201 is cooled down to partially cooled biomass 1202 by partially heated process water 1205. Partially heated process water 1205 recovers thermal energy form the hydrolyzed biomass 1201 and becomes heated process water 1206 to be used in biomass preheating before hydrolysis. Next the partially cooled biomass 1202 is pumped by pump 1207 to heat exchanger B 1211 where it is cooled down to cooled biomass 1203 by process water in 1204. In the process in heat exchanger B 1211, the process water 1204 is warmed up to partially heated process water 1205. Control unit 1209 measures the temperature of cooled biomass 1203 and adjusts the heat transfer operation by setting the speed of pump 1207. If the cooled biomass 1203 is too warm, then the control unit 1209 sets the pump 1207 to lower speed to enable better heat transfer from biomass 1201 & 1202 to process water 1204 & 1205. If the cooled biomass 1203 is too cold, then the control unit 1209 sets the pump 1207 to higher speed to enable less heat transfer from biomass 1201 & 1202 to process water 1204 & 1205.

An example, the temperature of process water is 40° C. and the temperature of hydrolyzed biomass is 100° C. First the hydrolyzed biomass is cooled in heat exchanger A from 100° C. to close to 80° C., and the partially heated process water entering heat exchanger A is heated up from close 60° C. to close 80° C. in heat exchanger A. Next the partially cooled biomass is cooled down in heat exchanger B from close 80° C. to close 60° C. by process water which is heated up from temperature of 40° C. to close 60° C. Further cooling of the cooled biomass can be arranged by driving the pump at slower speed, using cooler process water (as an example 30° C.) or pumping cool water to anaerobic digester.

If the heat is transferred perfectly in the heat exchanger A the temperatures of heated process water to biomass preheating and partially cooled biomass are at the same temperature, close to 80° C. Also if the heat is transferred perfectly in the heat exchanger B, the temperatures of partially cooled biomass and partially heated process water are at the same temperature, close to 60° C. If only heat exchanger had been used, the temperatures of cooled biomass and heated process water would be close to 70° C.

Figure 13:
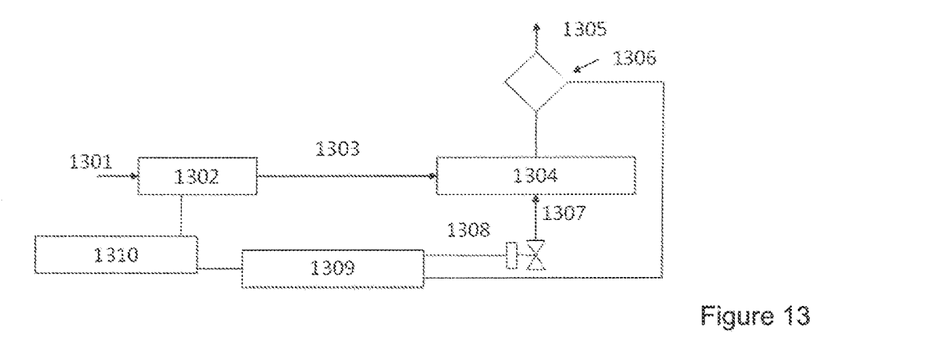
FIG. 13 illustrates a drying cycle for a system according to an embodiment.

FIG. 13 illustrates a drying cycle for a system according to an embodiment. The drying cycle may be performed in a dryer in the system of FIG. 1. The dryer may include a mechanical dryer 1302, a thermal dryer 1304 as described above. Biomass may be received to the dryer after digestion of the biomass in the digestion device. The received biomass may be first dried in the drying cycle by the mechanical dryer and after the mechanical dryer by the thermal dyer. The mechanical dryer and the thermal dryer form parts of the drying cycle, where each part dies the biomass for a specific time. The proportions of the mechanical drying part and the thermal drying part in the drying cycle are determined on the basis of humidity level of the biomass dried by the thermal dryer and/or available heat, e.g. steam, to the thermal dryer.

Both mechanical dryers 1302 and thermal dryers 1304 drying processes can be controlled separately to ensure desired humidity level in dried biomass 1305. Digested biomass 1301 is first dried in mechanical dryer 1302. After the mechanical dryer the partly dried biomass 1303 is transferred to thermal dryer 1304. In thermal dryer 1304 the partly dried biomass is dried until it reaches desired humidity level. Humidity level of the partly dried biomass is monitored by humidity sensor 1306. When desired dry matter level is reached, the drying cycle is finished and the dried biomass 1305 is released from the thermal dryer 1304. Control unit 1309 monitors the humidity level of the partly dried biomass 1303 via humidity sensor 1306. Control unit 1309 can adjust the control valve 1308 to control heat in 1307 which dries the partly dried biomass 1303 in the thermal dryer 1304. Control unit 1309 can also control mechanical dryer control unit 1310 to regulate the degree of drying process in mechanical dryer 1302 and the humidity level of partly dried biomass 1303.

An example, control unit 1309 monitors the humidity level of the dried biomass out 1305 by humidity sensor 1306, if the humidity level is at acceptable level, the control unit 1309 can adjust the amount of heat in 1307 by controlling the control valve 1308. If the humidity level in dried biomass out 1305 is at acceptable level, the control unit 1309 can restrict the amount of heat in 1307 by adjusting the control valve 1308 as far as the humidity in dried biomass out 1305 is at acceptable level, monitored by the humidity sensor 1306. That way thermal energy can be transferred to other purposes. If there is more heat in 1307 available than needed in thermal dryer 1304, the control unit 1309 may adjust the levels of mechanical and thermal drying. In that case control unit 1309 can drive mechanical dryer control unit 1310 to control the drying process in mechanical dryer 1302 to remove less humidity form the digested biomass 1301 and save electrical energy in mechanical drying process. The control unit 1309 can in that case adjust the control valve 1308 to let more heat in 1307 to perform acceptable drying result for the dried biomass out 1305 monitored by the humidity sensor 1306.

Figure 14:
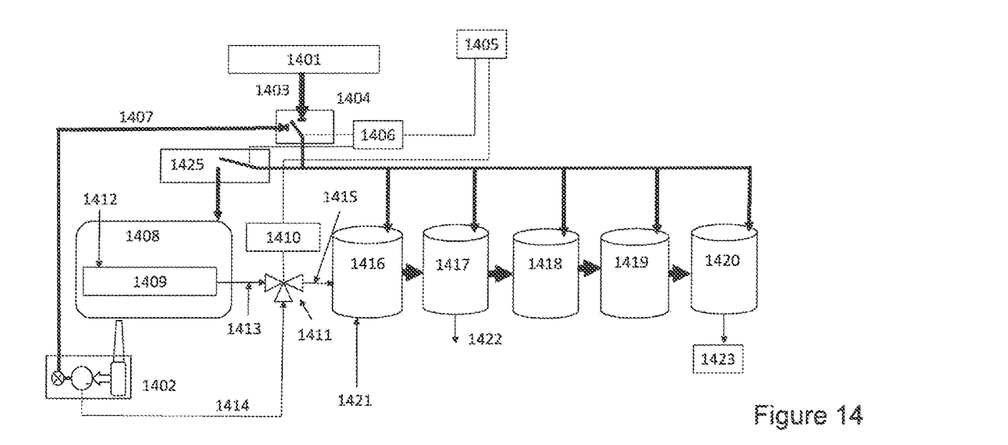
FIG. 14 illustrates control power for external sources of electrical energy, according to an embodiment.

FIG. 14 illustrates control power for external sources of electrical energy, according to an embodiment. The system may include a system of FIG. 1, and include a CHP device 1402, hydrolysis device 1416, anaerobic digestion device 1417, mechanical dryer 1418, thermal dryer 1419 and pelleting machine 1420. The system may include an interface to an external energy source. The external energy source may be the electrical grid, a windmill or a solar energy plant.

FIG. 14 illustrates a system and method for control power, where traffic fuel, heat and electricity are produced by a combined heat and power plant fueled by dried biomass, and/or by heat and electricity obtained from an external source of energy. The system can be run partly of fully by electricity from the external energy source; for example because of the need to process biomass and produce biofuels during a CHP maintenance break, during startup phase of the system prior to the self-sufficient phase of operation or when operating as control power provider with external energy providers, such as wind power park or a solar power park and utilizing their excess electricity production during a production peak. The system can be co-located with an external energy provider or it can be connected to the external energy provider by an electric grid.

The system may have at least two operating modes including a self-sufficient mode of operation, where production of traffic fuel, heat and electricity is provided by energy obtained from batches of raw biomass received to the process and processed into dried biomass, e.g. pellets for fueling the CHP plant, and an control power provider mode of operation, where the production of traffic fuel, heat and electricity is provided by energy obtained from an external energy source, for example a source of electrical energy. The processing of the raw biomass for the self-sufficient mode of operation has been described in the above embodiments, for example in FIG. 4. It should be appreciated that energy may be obtained for the traffic fuel, heat and electricity production using both the self-sufficient mode of operation and the control power provider mode of operation, whereby the CHP plant may produce heat and electricity from the processed dried biomass and the external energy source may be used to produce heat and electricity. In the following, the system is described in a more detailed example.

When working in the control power provider, mode the CHP device 1402 is providing no or only partly the CHP heat 1414 and CHP electricity 1407. When energy is not produced or only partly produced, then an external electrical energy source 1401 is connected to the system by input electricity switch 1404 which is operated by control relay 1406, which is controlled by control unit 1405.

When the system is set to run by external electrical energy source 1401, the control unit 1405 controls control relay 1406, control relay 1410 and boiler switch 1425.

When the control unit 1405 drives the control relay 1406 to operate the input electricity switch 1404 to switch on the external electricity 1403, then external electricity provided electrical energy 1403 is provided to the electrical boiler 1408, hydrolysis device 1416, anaerobic digestion device 1417, mechanical dryer 1418, thermal dryer 1419 and pelleting machine 1420.

When operating on external electricity 1403, the control unit 1405 switches on the boiler switch 1425 to provide electricity to the electrical boiler 1408, where electrical heating device 1409 heats up the water 1412 to produce external energy provided heat 1413. The electrical boiler 1408 can also be integrated to the hydrolysis device 1416.

Control unit 1405 drives control relay 1410 to operate the heat 3-way valve 1411, which connects the external energy provided heat 1413, as thermal energy to hydrolysis 1415, to hydrolysis device 1416.

When operating on external electricity 1403 the systems operates in the normal way by processing biomass 1421 in hydrolysis device 1416, in anaerobic digestion device 1417, in mechanical dryer 1418, in thermal dryer 1419 and in pelleting machine 1420 producing biogas 1422 and solid biofuel or pellets 1423 to be used later as control power in the CHP device 1402 to produce CHP heat 1414 and CHP electricity 1407 or used otherwise.

To run the system on fully external electricity source 1401 and on no CHP heat 1414 and no CHP electricity 1407, the control unit 1405 operates the control relay 1406 to drive the input electricity switch 1404 to switch off the CHP electricity connection 1407. Then the control unit 1405 also switches off the CHP heat 1414 by driving the control relay 1410 to operate the heat 3-way valve 1411.

When CHP unit 1402 is taken back to use, the control unit 1405 drives the control relay 1406 to operate the input electricity switch 1404 to switch on CHP electricity 1407 and switch off the external electricity 1403 input. The control unit 1405 drives also the control relay 1410 to switch on the CHP heat 1414 and switches off the external energy provided heat 1413 and closes the boiler switch 1425.

It should be appreciated that one or more controllers described in FIG. 8 may be used to implement the system and method described in the embodiments.

Systems such as biomass processing system, renewable energy power plants and traffic fuel production units and/or other corresponding devices, systems or apparatuses implementing the functionality of a system, device or unit described with an embodiment comprise not only prior art means, but also means for a) receiving raw biomass into the hydrolysis device, b) feeding biomass processed by the hydrolysis device to the digestion device, c) feeding biogas obtained in the digestion device to the traffic fuel production unit, d) recovering heat from the hydrolysis device, e) drying biomass processed by the digestion device by the heat recovered from the hydrolysis device, f) recovering heat from the dryer, g) feeding heat recovered from the dryer to the hydrolysis device to be used in pre-heating of the received raw biomass, h) feeding heat recovered from the dryer to the district heating (106*a*), i) fueling production of electricity by the dried biomass from the dryer.

More precisely, they comprise means for implementing functionality of a corresponding apparatus or system described with an embodiment and they may comprise separate means for each separate function, or means may be configured to perform two or more functions.

The techniques and methods described herein may be implemented by various means. For example, a controller for a system according to an embodiment may be implemented by one or more processors, microprocessors, other electronic units designed to perform the functions described herein, or a combination thereof, for example a computer unit. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the arrangement described herein may be rearranged and/or complemented by additional components in order to facilitate the achievements of the various aspects, etc., described with regard thereto, and they are not limited to the precise configurations set forth in the given figures, as will be appreciated by one skilled in the art.

Thus, according to an embodiment, the system may comprise processing means configured to carry out the functionalities described in any of the above embodiments. In an embodiment, at least one processor, memory and a computer program code form an embodiment of processing means for carrying out the embodiments of the invention.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment.

It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A method of processing biomass by a system comprising a combined heat and power plant, an interface for feeding biogas to a traffic fuel production unit, interfaces to a district heating system and an electrical grid, and a hydrolysis device, a digestion device, a dryer and a heat recovery unit, which are operatively coupled for transferring heat, intermediate products and final products of the process, wherein the method comprises:
   a) receiving raw biomass into the hydrolysis device;
   b) feeding biomass processed by the hydrolysis device to the digestion device;
   c) feeding biogas obtained in the digestion device to the traffic fuel production unit;
   d) recovering heat from the hydrolysis device;
   e) drying biomass processed by the digestion device by the heat recovered from the hydrolysis device;
   f) recovering heat from the dryer;
   g) feeding heat recovered from the dryer to the hydrolysis device to be used in pre-heating of the received raw biomass;
   h) feeding heat recovered from the dryer to the district heating;
   i) fueling production of electricity by the dried biomass from the dryer.

2. A method according to claim 1, wherein a plurality of successive batches of biomass are processed, and the hydrolysis is performed in a plurality of successive phases for each of the batches of biomass, such that an early phase of the hydrolysis of one batch is heated by heat recovered form a later phase of the hydrolysis of another batch.

3. A method according to claim 1, wherein the hydrolysis is performed in a plurality of successive phases defined by temperatures, wherein the temperatures of the phases increase from a first phase to the last phase.

4. A method according to claim 1, wherein a plurality of successive batches of biomass are processed, and the hydrolysis is performed in a plurality of successive phases for each of the batches of biomass, said successive phases comprising a first phase heated by heat recovered from the combined heat and power plant; a second phase heated by heat recovered from a second phase of the hydrolysis, and a third phase heated by excess heat recovered from the combined heat and power plant, said excess heat recovered from the combined heat and power plant before a turbine for generating electricity.

5. A method according to claim 1, wherein the biomass is sterilized by the hydrolysis device by heat from the combined heat and power plant.

6. A method according to claim 1, wherein heat is recovered from a batch of biomass processed by the hydrolysis device and a next batch of biomass is heated by the recovered heat from the batch processed by the hydrolysis device, wherein the processed biomass by the hydrolysis device is cooled and fed to the digestion device.

7. A method according to claim 1, wherein a batch of the biomass is processed by the digestion device, and a weight of the batch and humidity of the biogas output from the digestion device are measured for determining termination of the digestion of the biomass.

8. A method according to claim 1, comprising:
recovering heat from the combined heat and power plant after a turbine for producing electricity; and
feeding the recovered heat to the dryer.

9. A method according to claim 1, comprising:
obtaining water vapor from a batch of biomass being treated by the dryer and feeding the water vapor to heat a next batch of biomass entering the dryer.

10. A method according to claim 1, wherein the biomass processed by the digestion device is dried by a drying cycle comprising a mechanical drying and thermal drying parts, and the proportions of the mechanical drying part and the thermal drying part in the drying cycle are determined on the basis of humidity level of the biomass dried by the thermal dryer and/or available heat to the thermal dryer.

11. A method according to claim 1, wherein traffic fuel, heat and electricity are produced by the combined heat and power plant fueled by the dried biomass, and/or by heat and electricity obtained from an external source of energy.

12. A method according to claim 1, wherein at least a portion of the dried biomass is pelletized for fueling the combined heat and power plant.

13. A method according to claim 1, wherein excess heat is obtained and fed to the district heating system.

14. A system for processing biomass, comprising a combined heat and power plant, an interface for feeding biogas to a traffic fuel production unit, interfaces to a district heating system and an electrical grid, and a hydrolysis device, a digestion device, a dryer and a heat recovery unit, which are operatively coupled for transferring heat and intermediate and final products of the process, wherein the system is caused to:
 a) receive raw biomass into the hydrolysis device;
 b) feed biomass processed by the hydrolysis device to the digestion device;
 c) feed biogas obtained in the digestion device to the traffic fuel production unit;
 d) recover heat from the hydrolysis device;
 e) dry biomass processed by the digestion device by the heat recovered from the hydrolysis device;
 f) recover heat from the dryer;
 g) feed heat recovered from the dryer to the hydrolysis device to be used in hydrolysis of biomass;
 h) feed heat recovered from the dryer to the district heating; and
 i) fuel production of electricity by the dried biomass from the dryer.

15. A system according to claim 14, wherein the system:
comprises a selector for selecting one or more operational parameters of the system on the basis of type of biomass.

16. A system according to claim 14, wherein the selector determines characteristics of heat flow between at least one of: parts of the system and batches of biomass processed by the system.

17. A system according to claim 14, comprising a humidity sensor, a weight sensor, a pH-sensor and/or a pressure sensor, a temperature sensor operatively coupled to one or more of the hydrolysis device, heat recovery unit, digestion device, dryer and interfaces, for monitoring corresponding limits in batches of biomass processed by the system.

18. A system according to claim 14, comprising a steam dome connected to an output valve of the hydrolysis device such that heat may be recovered from the hydrolysis process.

19. A system according to claim 14, comprising a controller connected to the hydrolysis device, the heat recovery unit, the digestion device, the dryer and the interfaces for operating the system, wherein the hydrolysis device includes a biomass output valve for transferring treated biomass out of the hydrolysis device, and a heat output valve for recovering heat from the hydrolysis device, wherein the controller and the hydrolysis device are caused to:
 open the heat output valve;
 open, after opening the heat output valve, the biomass output valve.

20. A system according to claim 19, wherein the biomass output valve is opened after determining a decrease of pressure level within the hydrolysis device.

21. A system according to claim 14, wherein at least one of the hydrolysis device, heat recovery unit, digestion device and dryer are thermally isolated.

* * * * *

UNITED STATES PATENT AND TRADEMARK OFFICE
CERTIFICATE OF CORRECTION

PATENT NO.         : 10,041,035 B2
APPLICATION NO.    : 15/511079
DATED              : August 7, 2018
INVENTOR(S)        : Petteri Salonen Page 1 of 1

It is certified that error appears in the above-identified patent and that said Letters Patent is hereby corrected as shown below:

In the Claims

At Column 18, Line 44, "recovered form" should be -- recovered from --.

Signed and Sealed this
Twenty-second Day of January, 2019

Andrei Iancu
*Director of the United States Patent and Trademark Office*